(12) United States Patent
Kopelman et al.

(10) Patent No.: US 7,347,688 B2
(45) Date of Patent: Mar. 25, 2008

(54) DENTAL TARGETTING DEVICE AND METHOD

(75) Inventors: Avi Kopelman, Ramat Chen (IL); Eldad Taub, Reut (IL)

(73) Assignee: Cadent Ltd., Or Yehuda (IL)

( * ) Notice: Subject to any disclaimer, the term of this patent is extended or adjusted under 35 U.S.C. 154(b) by 211 days.

(21) Appl. No.: 11/105,355

(22) Filed: Apr. 14, 2005

(65) Prior Publication Data

US 2005/0233276 A1 Oct. 20, 2005

Related U.S. Application Data

(60) Provisional application No. 60/562,316, filed on Apr. 15, 2004.

(51) Int. Cl.
*A61C 3/00* (2006.01)
*A61C 7/00* (2006.01)

(52) U.S. Cl. .............................. 433/24; 433/3

(58) Field of Classification Search .................... 433/6, 433/3, 215
See application file for complete search history.

(56) References Cited

U.S. PATENT DOCUMENTS

| | | |
|---|---|---|
| 3,686,762 A | 8/1972 | Sutter |
| 4,160,322 A | 7/1979 | Frazier |
| 4,183,141 A | 1/1980 | Dellinger et al. |
| 4,360,341 A | 11/1982 | Dellinger |
| 4,424,029 A | 1/1984 | Maijer et al. |
| 4,478,576 A | 10/1984 | Maijer et al. |
| 4,501,554 A | 2/1985 | Hickham |
| 4,626,208 A | 12/1986 | Hall |
| 4,812,118 A | 3/1989 | Creekmore |
| 4,850,864 A | 7/1989 | Diamond |
| 5,011,405 A | 4/1991 | Lemchen |
| 5,368,478 A | 11/1994 | Andreiko et al. |
| 5,542,842 A | 8/1996 | Andreiko et al. |
| 5,863,198 A | 1/1999 | Doyle |
| 5,879,158 A | 3/1999 | Doyle et al. |
| 5,971,754 A | 10/1999 | Sondhi et al. |
| 5,975,893 A | 11/1999 | Chishti et al. |
| 6,123,544 A | 9/2000 | Cleary |
| 6,334,772 B1 | 1/2002 | Taub et al. |
| 6,447,291 B2 | 9/2002 | Kim |
| 2003/0190575 A1 | 10/2003 | Hilliard |
| 2003/0224310 A1 | 12/2003 | Andreiko |
| 2004/0166462 A1 | 8/2004 | Phan et al. |
| 2004/0229185 A1 | 11/2004 | Knopp |

FOREIGN PATENT DOCUMENTS

WO 99/34747 A1 7/1999
WO 03/092532 A1 11/2003

*Primary Examiner*—Cris Rodriguez
*Assistant Examiner*—Candice C Stokes
(74) *Attorney, Agent, or Firm*—The Nath Law Group; Jerald L. Meyer; Matthew J. Moffa

(57) ABSTRACT

A targeting device and method enables one or more orthodontic elements to be aligned with and bonded onto at least one tooth in a predetermined manner. The device is in the form of a shell that has, for each tooth with respect to which it is desired to align an orthodontic element, a cavity shaped to receive the tooth. Targeting indicators are also provided, and are configured for enabling the corresponding orthodontic elements to be guided into alignment in the required predetermined manner with respect to a tooth that is received in a corresponding cavity.

18 Claims, 7 Drawing Sheets

Section Y-Y

DENTAL TARGETING DEVICE AND METHOD

This application claims the benefit of prior U.S. provisional application Ser. No. 60/562,316 filed Apr. 15, 2004 the contents of which are hereby incorporated by reference in their entirety.

FIELD OF THE INVENTION

This invention relates to a method and apparatus for bonding orthodontic appliances to teeth, in particular for enabling such appliances to be precisely positioned with respect the teeth.

BACKGROUND OF THE INVENTION

Orthodontics is the branch of dentistry dealing with teeth irregularities and their corrections, such as by means of braces. The primary purpose of orthodontic treatment is to alter the position and reorient an individual's teeth so as to modify or improve their function. Teeth may also be reoriented mainly for cosmetic reasons.

In orthodontic treatment, as currently practiced, it is necessary to affix various orthodontic components to the surfaces of a patient's teeth. (In this specification, we shall only refer to brackets as the orthodontic element or component to be anchored on a tooth's surface, but it is to be understood that this is only by way of example, and the invention applies to all other types of orthodontics elements, mutatis mutandis, such as for example tubes, springs and other appliances.) The location of the bracket on the tooth as well as its orientation is a critical factor in determining the direction of movement of the teeth during the treatment, and accurate placement may ensure that the teeth are aligned with a single bracket bonding treatment. Conversely, less accurate placement of brackets may require repeated treatments, including repeated bonding and wire bending procedures until the final alignment is achieved.

Brackets affixed to teeth surfaces serve to support wires and tensioning springs to exert moments of force acting to move the teeth subjected to these forces to a degree and in a direction causing the teeth to assume a desired posture in the dental arch.

In current orthodontic practice, the orthodontist decides on a general scheme of placing the brackets on the teeth and then attaches each of them to the surface of a tooth, in an exact location and orientation previously decided. Preparatory to an orthodontic treatment, the orthodontist typically prepares a plaster model of the teeth of the treated individual and on the basis of such model, the general scheme of placement of the brackets can be decided. Also, bracket manufacturers typically propose a particular placement position for their brackets, for example that the brackets should be placed within a certain distance from the gingival margin. Such proposals are based on average shapes and sizes of teeth.

A typical treatment plan includes, among other factors, the desired position of each of the force-inducing orthodontic implements on the teeth. The placement of the brackets on the teeth determines the outcome of the above-mentioned movements, e.g. the degree and direction of the teeth movements. Any deviation from the planned position of the brackets affects the outcome of the treatment. Thus, during the process of placing the brackets on the teeth, much effort is made to ensure the accurate positioning of the brackets in accordance with their desired position as determined by the treatment plan.

The brackets are typically placed on the buccal surface of the teeth. At times, it is desired both from a treatment perspective as well as for reasons of external appearance of the individual, to place the brackets on the lingual surface of the teeth. However, by current methods it is difficult to properly position the brackets on the lingual surfaces, particularly in view of difficulties in monitoring the position during attachment of the brackets.

Typically, the following general steps are conducted for properly positioning an orthodontic element such as a bracket on a tooth surface, and then fixing the bracket thereto:

Step I: The orthodontist brings the element, being held by the positioning tool, into proximity of the tooth;

Step II: The orthodontist then positions the orthodontic element on the tooth surface at the site coinciding with its intended position, and disengages it from the positioning tool.

Step III: Finally, the element is affixed to the designated site by a bonding agent.

Special tools are sometimes used for placing the brackets on the teeth, for example as described in U.S. Pat. No. 3,686,762, U.S. Pat. No. 4,424,029, U.S. Pat. No. 4,478,576 and U.S. Pat. No. 6,447,291.

Typically, the bonding of the bracket to the tooth is achieved by using either chemical adhesives or light curing adhesives. Chemical adhesives are typically cured by themselves. The curing begins as the adhesive coming in contact with the tooth surface is completely cured after some self-working time (typically about 1 to 3 minutes).

The difficulty with manual orthodontic procedures, as commonly practiced nowadays, is that they are subject to human error. In the first place, it is very hard to place the bracket where it is desired to be located. Another common difficulty relates to the disengagement of the bracket from the positioning tool, as this process typically causes a slight movement of the bracket on the tooth due to inherent and uncontrolled small human movements.

This difficulty is compounded when the orthodontist must place brackets not only on buccal tooth surfaces but also on lingual surfaces. With existing methods, it is not easy for an orthodontist to properly position brackets on lingual surfaces.

These difficulties are obviated in part by methods disclosed in U.S. Pat. No. 6,334,772 and the systems and devices disclosed therein to carry out these methods. In a preferred method disclosed in this patent, an orthodontic element such as a bracket is properly positioned on a tooth surface, and then the bracket is fixed thereto. A video camera continuously captures an image of the tooth or the element while the orthodontist brings the element into proximity of the tooth using a positioning appliance, and a video monitor displays a real-time image, together with indicators affording information in regard to the position intended for the orthodontic element on the tooth surface. Guided by these indicators, the orthodontist then positions the orthodontic element on the tooth surface at a site that coincides with its intended position, and finally, the element is affixed to this site by a bonding agent.

In WO 03/092532, a positioning appliance adapted to facilitate an orthodontics procedure in which a bracket or other orthodontic component is placed at a desired site on the surface of a tooth and affixed thereto. The appliance in this case comprises a hand-held tubular wand that has a protective sleeve section and a camera section telescoped in the sleeve section. A window is mounted at the front end of the sleeve section and a finger projecting therefrom is adapted to hold the bracket at a position abutting the tooth surface. A camera is housed in the camera section to capture through the window an image of the bracket on the surface of the tooth. One or more light sources are housed in the camera section, for irradiating the bracket and the tooth surface with light detectable by the camera. Additional one or more light sources are housed in the camera section and are capable of irradiates light at a wavelength that can cure an adhesive used for affixing the bracket or other orthodontic component to the surface of a tooth.

A more traditional form of positioning brackets is known as indirect bonding, and is based on forming a tray of a thermoplastic material over a physical model of the teeth on which the brackets have been positioned using a relatively weak adhesive. The brackets may be positioned onto the model in any one of a number of ways, for example as disclosed in U.S. Pat. No. 4,812,118. The tray thus comprises a negative impression of the teeth model, which is very close-fitting with respect thereto, and also has the brackets embedded in position in the tray in their correct positions with respect to the model. The tray can then be removed from the model, taking with it the brackets in the correct relative positions with respect to the negative impressions. The tray is then transferred to the intraoral cavity of the patient, and when properly fitted over the appropriate arch, presents the brackets in ostensibly the correct positions vis-à-vis the teeth. The brackets are simultaneously bonded onto the teeth, which requires all the teeth to be dry and pre-etched, and the tray may then be removed, leaving the brackets in place. This method is commonly practiced, and can be used for both buccal and lingual brackets. Most of the preparatory work is done by a technician rather than the dentist, and the technique results in a shorter installation time than when the brackets are installed manually one at a time, but the technician needs to have a supply of brackets readily available. On the other hand, should one or more of the brackets move during installation, or not be fixed properly onto the teeth, it has to be reset manually without the aid of the tray. In practice, many failures occur due to the imperfect fit between the tray and the teeth, resulting in part due to the dimensional differences between the plaster model and the actual teeth.

Of general background interest, the following references disclose tray-based orthodontic methods and devices.

In U.S. Pat. No. 5,971,754 adhesive is provided in two components, one applied to the teeth and the other to the bracket while embedded in the tray. When the two components come together, a bond forms within a short time period to enable removal of the tray without significantly changing the position of the appliance.

In U.S. Pat. No. 4,501,554, a second, rigid tray is inserted over a first traditional tray that carries the brackets, for stablising the seating of the brackets during seating or drying of the cement securing the brackets.

In U.S. Pat. No. 4,360,341, a variation of the traditional transfer tray is provided, in which the brackets are held in the tray by bracket orienting modules, providing positioning accuracy of the brackets.

In U.S. Pat. No. 6,123,544, brackets are held on arms that are connected to a transfer tray is provided. The arms are aligned with respect to a plaster model of the teeth, and the tray is formed over the arms. The arms are slid away from the model teeth and the assembly is removed from the plaster model. The assembly is then placed into the intraoral cavity, and the arms are retracted into the tray enabling the brackets to contact the teeth at the predetermined positions, where they can be bonded onto the teeth at the contact points. As with the traditional indirect bonding technique, dimensional inaccuracies between the model and the real teeth can lead to inaccurate placement.

In U.S. Pat. No. 5,975,893, aligner-based therapy philosophies and digital imaging/computer-driven rapid prototyping methods are combined, in which a set comprising a plurality of tray-shaped aligners are formed for a patient. Each upper and lower set of aligners (where required) is worn for a period of time. Each aligner in the set biases a patient's teeth toward an ideal occlusion more aggressively than the previous aligner, and typically between 15 to 25 progressive aligners may be used in one treatment. Over a period of time, the sequential and progressively biased positioners move teeth from their initial malccluded positions to a near finished and corrected state. Each aligner appliance generally comprises a U-shaped tray or shell having a trough that fits over the teeth. The tray is formed by sucking a thermo-formable sheet material over the reset stone model of the patient's dentition, using heat, pressure and a vacuum force, simultaneously. A first initial data set corresponding to the patient's current dentition is determined using a scanning technique. A final digital model of the dentition in its desired set up after treatment is designed. Intermediate digital models between the initial and final models are then created, and positive tooth models are fabricated from the digital models using rapid prototyping techniques. A conventional pressure or vacuum molding machine is used to produce the appliances from each of the positive tooth models.

U.S. 2003/0190575 employs orthodontic aligner elements that are secured to openings in a removable aligner appliance in the form of a tray to exert the desired forces on selected teeth. This enables aligners to be used in the treatment of some orthodontic cases. In addition, the aligner elements are removable or adjustable, and when fitted in the tray, enable the forces to be maintained, changed, or reactivated over the course of treatment.

In U.S. Pat. No. 4,183,141 a rigid cap is formed over the crowns of an idealized model of an arch, and a hollow guide element is fixed with respect to each of the teeth requiring a bracket. Brackets are held at the end of members, each of which slides in the corresponding guide element from a retracted position distanced from the teeth to a deployed position such as to abut the teeth, when the cap is transferred to the patient's arch. In U.S. Pat. No. 5,011,405, U.S. Pat. No. 5,368,478 and U.S. Pat. No. 5,879,158 a digital model of the intraoral cavity is created, and the shape of a positioning device such as a jig is calculated. In U.S. Pat. No. 5,542,842, U.S. Pat. No. 5,863,198, U.S. Pat. No. 4,626,208, U.S. Pat. No. 4,850,864 and U.S. 2003/0224310 various jig configurations are disclosed for positioning brackets with respect to teeth.

SUMMARY OF THE INVENTION

The term "position" is used herein to denote either the element's location on the surface of a tooth, its orientation or a combination of location and orientation. The term "positioning" will be used to denote the act of placing the bracket on the surface of a tooth in a desired position. The term "element" is used herein to denote a device which is fixed on to a tooth within the framework of an orthodontic treatment, e.g. a bracket.

The present invention relates to a targeting device for enabling one or more orthodontic elements to be positioned with respect to at least one tooth in a predetermined manner and bonded thereonto at such a position, comprising:— a shell comprising, for the or each tooth with respect to which it is desired to align a said orthodontic element, a cavity shaped to receive the tooth, and further comprising targeting indicators configured for enabling the corresponding said orthodontic element to be guided into alignment in said predetermined manner with respect to a said tooth that is received in a corresponding said cavity.

The said predetermined manner comprises a spatial orientation and typically includes a predetermined position and a predetermined orientation with respect to a corresponding tooth surface of a said tooth.

In some embodiments, the targeting indicators are associated with windows comprised in said shell, each window extending from an outside of said shell to a corresponding said cavity. In one such embodiment, each said window is configured for enabling the corresponding orthodontic element to be attached to a corresponding said tooth surface. In particular, each said window is configured for enabling the corresponding orthodontic element to subsequently remain attached thereat in the absence of said device. Preferably, each said window is sufficiently large to provide a clearance with respect to a said orthodontic element that is targeted via said window. Each said window is configured for enabling a corresponding said orthodontic element to be positioned in said predetermined manner with respect to a surface of a tooth in a non-engaging manner with respect to the shell.

In some embodiments, and for at least one window, at least a part of the periphery of said window comprises said target indicators, wherein said target indicators are in the form of visual markings with respect to which predetermined reference datums on a corresponding said orthodontic element are to be aligned. Also for at least one said window, the window may be of a shape indicative of the said manner in which the corresponding said orthodontic element is to be fixed with respect to the corresponding tooth surface. Such a window may be in the shape of a targeting mark, for example in the form of an "X" or a "+" symbol.

In some embodiments, for at least one window, at least part of the edges of said window comprise said target indicators, wherein said parts of said edges are of a shape substantially complementary to the plan profile of corresponding parts said orthodontic element. Advantageously, the window comprises a slot extending to a free edge of said shell corresponding to the gingival margin of a tooth for which the corresponding cavity is designed.

In another embodiment, the said target indicators are provided in at least one said cavity and interact with a tooth that is received in said cavity such as to mark thereon the said desired manner in which it is desired to align a said orthodontic element with respect to the tooth. Such target indicators may comprise a transfer patch having a form correlated to said predetermined manner, such that when a tooth is received in said cavity, the transfer patch transfers a material to said tooth, wherein the shape of said transferred material is correlated to the desired manner in which it is desired to align the corresponding orthodontic element. The transfer patch may be configured to transfer a sticker, or colored pigment, or etching material of predetermined shape to a tooth received in said cavity. Alternatively, the target indicators comprise a protrusion having a form correlated to said predetermined manner, such that when a tooth is received in said cavity, the protrusion can form marks on the surface of the tooth in contact therewith, wherein the shape of said protrusions is such that the said marks are correlated to the desired manner in which it is desired to align the corresponding orthodontic element.

Typically, the said orthodontic elements comprise orthodontic brackets.

The present invention is also directed to a method for aligning and bonding one or more orthodontic elements with respect to at least one tooth in a predetermined manner, comprising:—

(A) providing target indicators for the or each tooth with respect to which it is desired to align a said orthodontic element, and for said each orthodontic element in turn:

(B) bringing said orthodontic element into proximity with corresponding said targeting indicators; and (C) aligning said orthodontic element with respect to said targeting indicators to achieve the required said alignment of the element with respect to the tooth accommodated in the corresponding said cavity.

Typically such a method comprises:—

(a) providing a shell comprising, for the or each tooth with respect to which it is desired to align a said orthodontic element, a cavity shaped to receive the tooth, and further comprising targeting indicators configured for guiding the or each said orthodontic element into alignment in said predetermined manner with respect to a said tooth that is received in a corresponding said cavity;

(b) seating said shell over said teeth such that the or each said tooth is received in a respective said cavity; and for said each orthodontic element in turn:

(c) bringing said orthodontic element into proximity with corresponding said targeting indicators; and (d) aligning said orthodontic element with respect to said targeting indicators to achieve the required said alignment of the element with respect to the tooth accommodated in the corresponding said cavity.

The said predetermined manner refers to a spatial disposition and typically includes aligning one or more said orthodontic elements with respect to said at least one tooth in a predetermined position and orientation.

In some embodiment, the targeting indicators are associated with windows comprised in said shell, each said window extending from an outside of said shell to a corresponding said cavity. In one such embodiment, step (d) comprises inserting a said orthodontic element into a said window into contact with a said tooth accommodated in the corresponding said cavity, wherein the shape, location and orientation of the window is complementary to the shape and desired location and orientation of the said orthodontic element with respect to the said tooth. The method further includes the step of bonding each said orthodontic element when aligned in said predetermined manner with respect to the corresponding tooth, and also the step of removing the said shell after the said orthodontic elements have been bonded to the teeth.

In another such embodiment, step (d) comprises marking the desired position and orientation of a said orthodontic element with respect to a said tooth accommodated in the corresponding said cavity by means of said corresponding window, wherein the location and orientation of the window is complementary to the shape and desired location and orientation of the said orthodontic element with respect to the said tooth. In this embodiment, the shape of the window is complementary to the shape of the orthodontic element that it is desired to align with respect to said tooth. The method further includes the step of removing the shell and aligning each said orthodontic element with the corresponding marked position on the corresponding tooth, and the step of bonding each said orthodontic element when aligned in said predetermined manner with respect to the corresponding tooth.

In another embodiment, the target indicators comprise a transfer patch having a form correlated to said predetermined manner, and wherein step (d) comprises transferring a transfer material to a said tooth that is accommodated in a corresponding said cavity, wherein the shape of said transferred material is correlated to the desired manner in which it is desired to align the corresponding orthodontic element. The transfer patch may transfers a sticker, colored pigment or etching material, for example, of predetermined shape to a tooth received in said cavity. Alternatively, the target indicators comprise a protrusion having a form correlated to said predetermined manner, and wherein step (d) comprises causing said protrusion to come into contact with a tooth accommodated in a corresponding said cavity and to form marks on the surface of the tooth in contact therewith, wherein the shape of said protrusions is such that the said marks are correlated to the desired manner in which it is desired to align the corresponding orthodontic element.

The method finds particular application with orthodontic brackets.

The invention will now be illustrated below by some non-limiting specific embodiments, with references to the figures in the attached drawings. The illustrated embodiments refer to positioning of a bracket, it being understood that the invention applies, mutatis mutandis also to positioning of other orthodontic elements.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 4 shows in cross-sectional view an improvement of the embodiment of FIG. 2a.

DETAILED DESCRIPTION OF THE INVENTION

Figure 1:
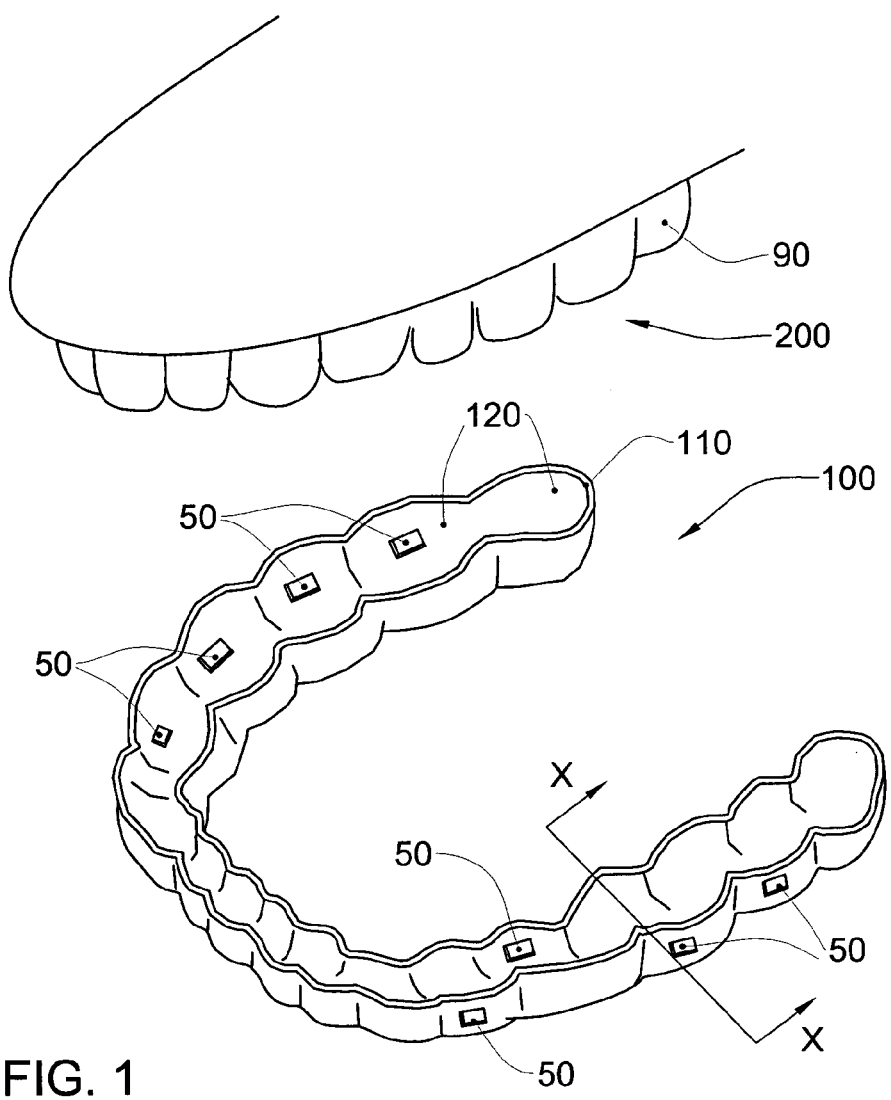
FIG. 1 is an isometric view of a first embodiment of the invention.

Referring to FIG. 1, a first embodiment of the present invention comprises a dental targeting device in the form of a tray, generally designated with the numeral 100, having a plurality of windows 50. The tray 100 comprises a U-shaped shell 110 having a plurality of cavities 120 which are shaped to receive teeth. As described in greater detail herein, the tray 100 is designed to fit over an arch 200 regarding which it is desired to provide an orthodontic treatment to at least some of the teeth therein. Thus, the inside shape of each of the cavities 120 is substantially complementary to the external shape of the particular tooth of the arch 200 that is received therein, in particular the lingual and buccal/labial surfaces of the teeth. Accordingly, the tray 100 is designed to fit over the teeth in their current positions, and does not itself require to exert any alignment forces on the teeth, even if manufactured from an elastic material.

Figure 2A:
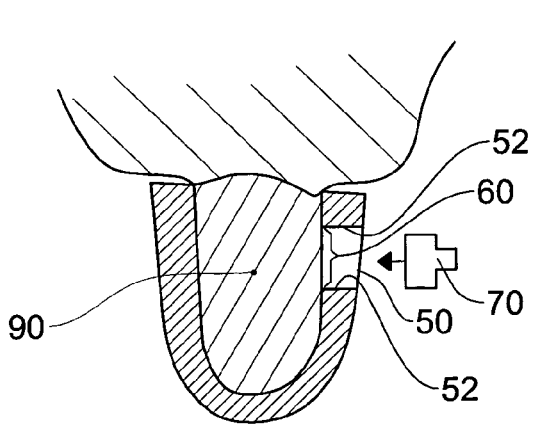
FIG. 2a shows in cross-sectional view the embodiment of FIG. 1 along X-X.
Figure 3A:
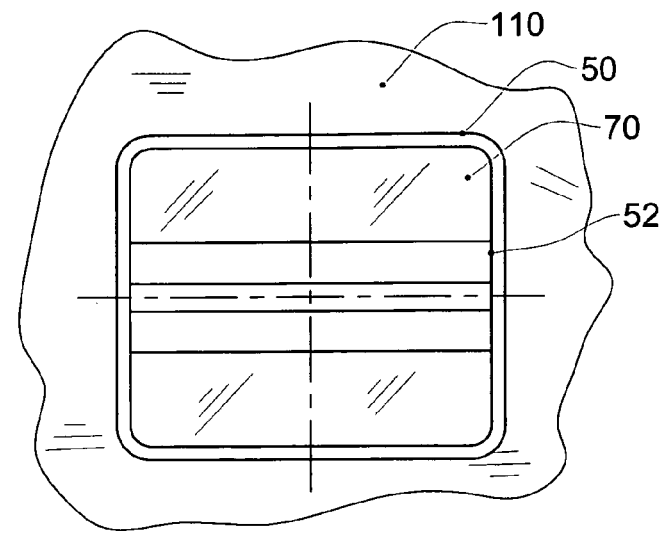
FIGS. 3a, 3b and 3c illustrate alternative window configurations for the embodiment of FIG. 1.

In this embodiment, when the tray 100 is properly seated over the arch 200, the windows 50 each expose a part 60 of a corresponding tooth 90 that is to receive a bracket 70. Thus, the windows 50 provide targets for enabling each of the brackets 70 to be properly positioned with respect to the teeth that they are to be bonded to. Each window 50 is appropriately shaped to enable a desired bracket 70 to be inserted therethrough from the outside and onto a tooth, as illustrated in FIG. 2a, and thus comprises target indicators in the form of all or some of the edges 52 of the window. The windows may be formed on the buccal/labial side or on the lingual side, or both sides of the cavities in tray 100, as required. In particular, and referring to FIG. 3a, the windows 50 are each of a shape and size substantially complementary to the shape and size of the desired bracket 70 that is to be fitted therethrough.

Figure 3B:
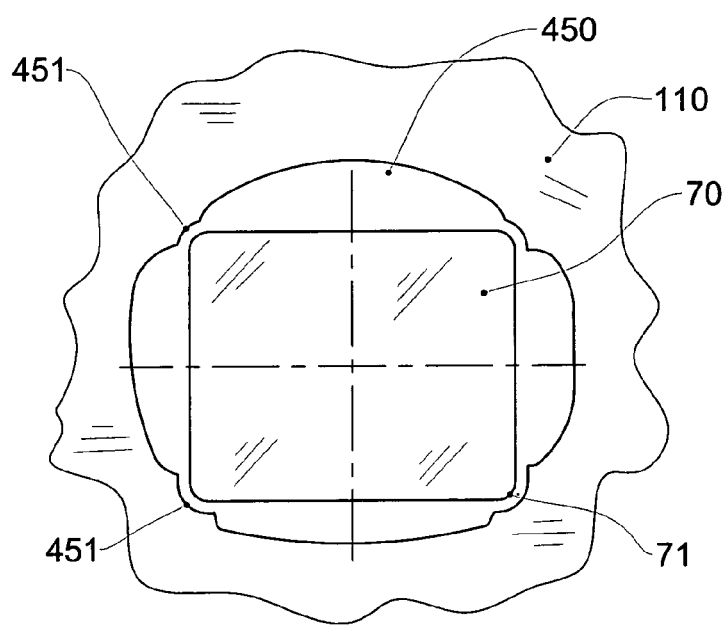

Optionally, and as illustrated in FIG. 3b, in a variation of the first embodiment, the window 450 may be designed to have a target indicators in the form of abutment points 451 or edges (not shown) against which the desired bracket can be abutted to positively fix the position of the bracket with respect to the tray 100. For example, the window comprises four corner abutment points 451 with respect to which the corners 71 of the bracket 70 can be positively located.

Figure 3C:
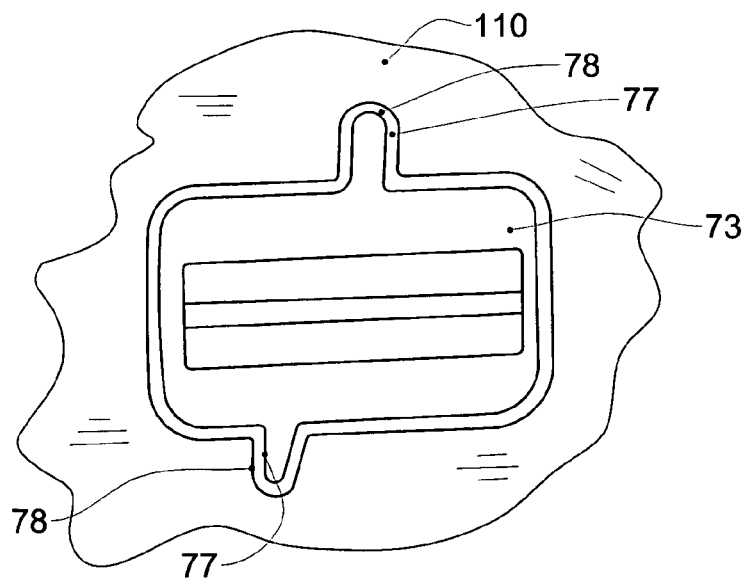

Alternatively, and as illustrated in FIG. 3c, the brackets 73 may be of a particular shape and/or have some feature such as a notch or protrusion 77 that can help to define some reference datums with respect to the bracket 73. Accordingly, the window may comprises a complementary feature, such as a notch 78 to complement protrusion 77. The bracket 73 can then be spatially located where desired by bringing together the complementary features 77 and 78, as illustrated in FIG. 3c.

Thus, each bracket 70 may be positively located on the corresponding tooth 90 via one of the windows 50 (or 450) in a position that is fixed relative to the shell 110 when the tray 100 is properly seated over the teeth of arch 200. Accordingly, the orientation of each of the windows, and the position of each window 50 with respect to the corresponding cavity 120 of the shell 110, are determined such as will expose the required parts 60 of the teeth on which it is desired to have bonded thereto the brackets 70. The size and shape of the windows 50 are also a little larger than those of the particular bracket 70 that is required to be targeted by the window 50, so that the window 50 does not actually engage the bracket 70. Although the bracket 70 typically abuts some or all of the edges or sides 52 of the window 50, there is sufficient clearance between the window 50 and the bracket 70 to enable the shell 110 to be removed from the arch 200 leaving the brackets behind, and in place on the teeth when they have been bonded thereto.

Figure 2B:
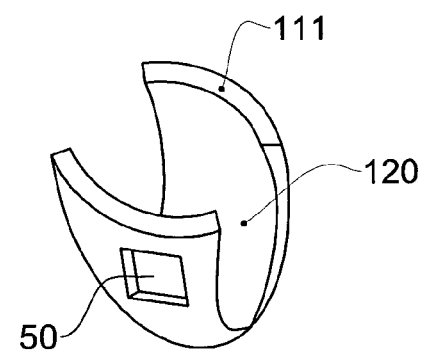
FIG. 2b shows in perspective view a portion of the tray of the embodiment of FIG. 1 corresponding to a single tooth.

Optionally, the tray 100 may be suitably marked, for example by ink or the like using a suitable printing method, or etched or otherwise marked to indicate the optimum paths along which to cut the tray 100 to enable the shell portion 111 comprising the part of cavity 120 corresponding to each individual tooth to be separated from the rest of the tray. Thus, referring to FIG. 2b, such a shell portion 111 may be used to target a bracket onto a particular tooth at almost any point during treatment, when possibly the teeth may have already moved to an extent that would not allow the tray 100 to be properly seated onto the teeth. Such a requirement may arise when a bracket falls off a tooth during the middle of an orthodontic treatment. Relative to the corresponding tooth, a particular bracket remains in the same position during the full duration of the treatment. Since the shell portion 111 comprises a cavity that substantially follows the shape of the tooth (particularly the buccal and labial sides thereof) that it is designed to fit over, the window 50 of the shell portion will remain in the appropriate place with respect to the tooth when the shell portion 111 is properly seated onto the appropriate tooth.

Figure 4:
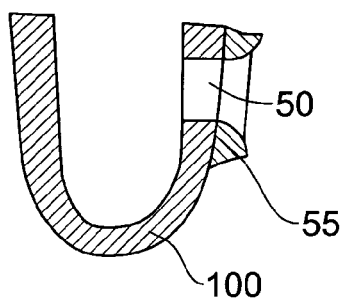

Optionally, and as illustrated in FIG. 4, the external periphery of the windows 50 may comprise a bellmouth entry structure 55 to facilitate aligning the brackets with the windows.

The target areas 60 for each tooth are previously identified, according to a set up plan provided by the orthodontist, as being appropriate for bonding the brackets onto the misaligned teeth of the arch 200 such that the teeth may be aligned in the manner desired in response to the orthodontic treatment.

Such set up plans may be provided in any number of ways. In the traditional manner, for example, a plaster model of the patient's dentition may be made, typically from an impression taken of the patient's arches, and the individual model teeth are sawed off the model, separated and then aligned as desired. Having the final dispositions of the teeth defined, a plurality of brackets can then be positioned on this aligned model corresponding to the final desired orientation of the brackets after the treatment. For example, when a straight wire orthodontic method is used, the brackets should be substantially aligned on a smooth arc circumscribing the arch 200. Then, the positions of the brackets with respect to each tooth can be mapped back to the original tooth model to provide the location and orientation of the brackets required on the patient's teeth, under the specific orthodontic treatment, to provide the desired alignment of the teeth.

Having constructed a physical plaster model of the arch 200, the desired position and orientation of the brackets are marked on the model, and this can be done, for example, by temporarily bonding the brackets to the model in the desired positions, for example in the manner used in traditional indirect bonding techniques, for example, which are known per se. Next, the position of each of the brackets may be marked by circumscribing each bracket with a sharp instrument such as to etch the periphery thereof on the model teeth. The brackets can then be removed, and their positions are clearly marked by the etched peripheries left on the model. Then, a tray 100 of transparent material is formed over the model in any suitable manner, for example as used in traditional indirect bonding techniques, comprising pressure or vacuum forming a suitable sheet material, such as 0.75 mm thermal forming dental material. Suitable materials include, for example, biocryl, by Great Lakes Orthodontics Ltd., Tonawanda, N.Y.

At this point the etched peripheries on each tooth are visible, and a suitable tool, such as for example a sharp or heated cutting tool, a punch, a laser or a power tool, may be employed to cut windows 50 in registry with the etched peripheries.

Alternatively, the position of a datum with respect to each bracket may be marked on the tooth model, for example as a "+" or "X" symbol or mark, such that the center of the mark corresponds to the center or other known location relative to the bracket, and the orientation of the mark is indicative of the orientation of the bracket, for example. Such a reference datum may be referred to a bracket centerline, bracket slot or any other convenient reference on the bracket by which it is possible to place the bracket in a desired position with some accuracy. Such symbols or marks may be provided manually, or by means of a suitable printer, such as for example a laser printer or inkjet printer or via any other suitable method that enables such symbols or marks to be formed on the tray 100. Printing by means of a printer is particularly useful in embodiments wherein the positions of the brackets are determined using a virtual model of the teeth, for example as described hereinbelow. Once the tray 100 is formed over the model, the marks are visible though the shell of the tray, if the tray is transparent. Then, windows 50 can be cut at the marks, according to the position and orientation thereof, in shapes and sizes corresponding to the shapes and sizes of the brackets that are intended to be positioned via the windows.

Alternatively, and particularly when the tray 100 is fabricated from a translucent or opaque material, pins may be attached to the teeth model at these datum positions, such that the pins project from the model teeth substantially orthogonally thereto. When the tray 100 is formed over the model, the pins project through the shell and thus provide a guide as to where the windows 50 are to be formed, and the windows may be cut out in a similar manner to that described above, for example. Optionally, two pins may be used for each bracket location: one pin fixes the position of the center of the bracket, while a second pin provides information regarding the orientation of the bracket at this position, for example.

Alternatively, the shell 110 may be formed over the model including the brackets in a similar manner to that known in the art, and the brackets 70 together with material of the shell in the vicinity thereof are subsequently removed from the shell 110 such as to form said windows 50. Using this method, the parts of the shell 110 on which the brackets 70 are attached have to be removed very carefully so that the windows 50 indeed permit subsequent aligning of the brackets.

Alternatively, computer based methods may be used for generating the set up. For example, in a first step, the three dimensional (3D) structure of the patient's dentition, including the teeth that are required to be moved during the course of the orthodontic treatment, and preferably the full dentition of the arch 200 on which these teeth are located, is determined, and provided in digitized form. Optionally both arches are scanned. This structure may be obtained in any number of ways. For example, the intra-oral cavity may be scanned or imaged using technology known in the art, including X-rays, CT, MRI, using direct contact methods or using non-contact methods such as for example those that employ an optical probe. Alternatively, a negative casting of a patient's teeth is obtained in a manner well known in the art, and this is used for preparing a positive cast suitable for scanning or imaging. Alternatively, the negative model itself is scanned or imaged. Alternatively, a composite positive-negative model may be scanned or otherwise imaged to obtain the desired 3D data. The dimensional data may be associated with a complete dentition, or of a partial dentition, comprising the teeth that are to be treated. Providing a digitized data set D1 from such scanning or imaging is also known in the art and will not be described further. The digitized data set D1 is manipulable, and thus allows the next step to be performed using a suitable computer.

In the next step, the data set D1 is manipulated to provide a final tooth arrangement comprising a final digitized data set D2, in which each tooth is positioned in the desired position, for example as described in WO 99/34747 or in U.S. Pat. No. 5,975,893, the contents of which are incorporated herein in their entirety. Essentially, the 3D data corresponding to the individual teeth, DT, of the scanned dentition are separated from one another, and the user repositions the DT data for each tooth based on visual appearance, using rules or algorithms, or according to prescriptions provided by the orthodontist.

In the next step, and based on the final data set D2, brackets are chosen and "virtually" positioned on the aligned teeth virtual model, and the corresponding positions of the brackets are then mapped back to the initial virtual model. The position and orientation of the brackets can be incorporated into the initial dataset D1.

Then, it is possible to manufacture a physical model of the teeth corresponding to D1, for example using CNC material removal techniques or rapid prototyping techniques, for example, and the tray 100 may then be manufactured as described above, mutatis mutandis.

Alternatively, and particularly when there exists a 3D numerical model of the teeth, it is possible to define three-dimensionally the positions of the brackets with respect to the 3D numerical model. The tray 100 may then be manufactured using CNC machining methods, for example, in which the tray 100 may be produced either indirectly or directly. Such indirect methods may comprise, e.g., manufacturing appropriate inner and outer molds using CNC techniques, and then applying an injection molding technique, for example, for producing a tray 100 from the molds. The inner mold comprises an external 3D structure substantially similar to that defined by dataset D1, and the outer mould may have an internal structure which is also similar to that defined by D1, but displaced thereof by a suitable material thickness to provide dataset D1'. Thus, the CNC machine used for such operations may be programmed to provide material removal passes over a blank of material, based on dataset D1, such as to provide the molds. The windows 50 may be integrally formed with the tray 100, or formed as a separated operation after the tray 100 is produced. Alternatively, the tray may be vacuum formed using only the positive mold thus produced.

A suitable direct method, on the other hand, may comprise any suitable material removal operation applied to a suitable material, and carried out using CNC machining techniques based on the datasets D1 and D1' of the numerical model. The windows 50 may be formed during the manufacture of the tray, or as a separate operation after the manufacture of the tray. Alternatively, the tray may be formed using other techniques such as described above, and the windows 50 may be formed using CNC machining techniques. In such a case, the spatial position and orientation of tray 100 as a whole must be known with respect to a machining datum so that machining operations are applied to the desired parts of the tray. If a plaster model of the teeth is available, this may be used for holding the tray steady while the windows are formed. Accordingly, it is possible to set the tray on a rig or chuck to hold the same in place, and thereafter scanned using a suitable 3D scanner. Alternatively, the tray 100 may be fabricated with indicia that help align the same with respect to predetermined datums in the CNC machine.

Alternatively, the tray 100 is fabricated using other methods. For example, the tray 30 may be fabricated using rapid prototyping techniques, for example based on a stereolithography machine, such as for example Model SLA-250/50 available from 3D System, Valencia, Calif., based on the dataset D1. A liquid or non-hardened resin is hardened into a 3D form that can be separated from the non-hardened liquid or resin to form a positive model of the arch 200 from the 3D numerical model thereof. Then, a tray 100 may be formed over the positive model in a similar manner to that described above, for example, Alternatively, an outer mold for the external surface of the tray 100 is produced in a similar manner to that described for the positive model, mutatis mutandis, and injection techniques are used to provide the tray 100 using the outer mold and the positive model.

The tray 100 is preferably made from a flexible material, but may also be made from a rigid or semi rigid material, including for example some rigid plastics, which may be easier to machine using CNC methods, for example.

It is thus possible for the tray 100 to be fabricated at one location, and then transported to another location where the windows 50 are formed, or for the finished tray 100 including windows 50 to be fabricated at a single location.

The windows 50 thus provided enable brackets 70 to be targeted and placed onto the desired areas 60 of the tooth model, and thus also of the patient's teeth when the tray 100 is properly seated thereonto. Optionally, the tray 100 may be suitably marked in the vicinity of each window 50 with an identifying mark, symbol or alphanumeric character, for example, that identifies the bracket 70 that is supposed to be targeted onto and bonded to the tooth via that window 50. Such an identifier may be printed, etched or in any other manner provided on the tray 100.

Each window 50 is thus formed for enabling a particular bracket to be brought into contact and required alignment with the required part 60 of the tooth where it is desired to bond the bracket to. Typically, such alignment comprises the spatial disposition of the bracket with respect to the corresponding tooth and includes the position and orientation of the bracket over the tooth surface. Thus, each window 50 is independent from the other windows. Accordingly, for any given tray 100, windows 50 therein can be formed to accommodate the same brand of brackets or alternatively a mixture of different brands of brackets, and/or brackets of different sizes, families or slot widths, and so on.

Placement of the brackets in the intraoral cavity can be effected in a number of ways. For example, the tray 100, having been manufactured to include windows 50 where desired therein, is seated onto the arch 200 so that each tooth thereof fits snugly within the corresponding cavity 120, leaving exposed parts 60 of the teeth. The orthodontist, or indeed any other care giver that is providing the orthodontic treatment, then takes each bracket 70 in turn and positions it in the appropriate window 50 so that the bracket 70 is guided by the window into alignment with the corresponding tooth, and abuts the part 60 of the corresponding tooth. Preferably, the part 60 of each tooth is etched prior to placement of the brackets to provide improved bonding with respect to the bracket 70. Etching can be performed as is known in the art, and it is possible to etch on each tooth a general area where it is known that will include the part 60. Alternatively, the part 60 is etched through the window 50. Alternatively, the position of the window 50 with respect to each tooth may be marked using any suitable marking device, such as a pen or a stamp for example, and the tray is removed, allowing the marked area to be etched. Prior to positioning the bracket, either the bracket 70 or the part 60 of the tooth, or both are coated with a suitable adhesive. The adhesive may be, for example, a chemical adhesive, and sets within a predetermined time period, and thus the tray 100 helps to maintain the brackets 70 in their desired positions until the adhesive sets, whereupon the tray 100 may be removed. Alternatively, the adhesive may be light cured, in which case the tray is preferably transparent to enable the brackets to remain in place while the adhesive is cured with light shone thereat from a suitable source.

Figure 5:
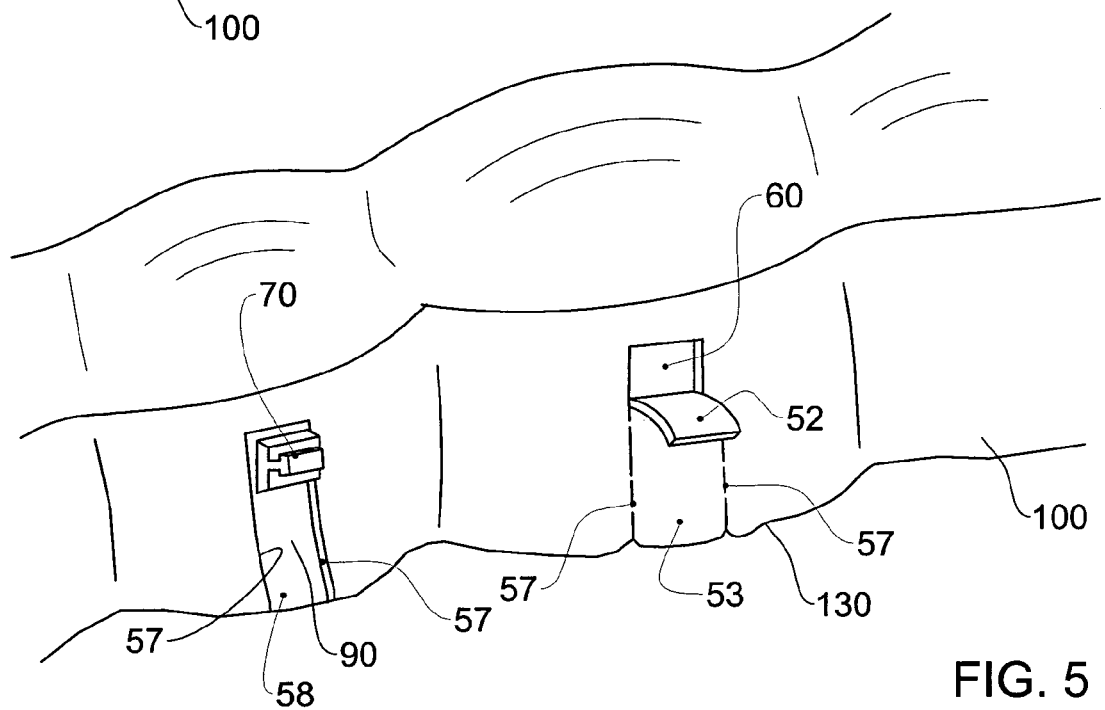
FIG. 5 illustrates in partial isometric view optional features for the embodiment of FIG. 1.

Once the adhesive has completely set, it is possible to remove the tray 100 from the arch 200. In embodiments where the tray 100 is made from a flexible material, the natural elasticity thereof enables the tray to be stretched over the brackets to enable the tray to be removed without interfering with the brackets. Optionally, though, the tray 100 may be cut, for example along the part thereof corresponding to the cusps of the teeth, to remove the tray 100 in two halves. Alternatively, and referring to FIG. 5, it is also possible to cut a strip 53 to form a slot 58 from the free edge 130 of the tray to the window 50 so that the tray may be lifted off the arch 200 in an interference-free manner with respect to the brackets 70. This slot 58 may be cut after the bracket 70 has been bonded in position. Alternatively, the tray 100 may comprise fracture lines 57 along the edges of the slot, to enable the strip 53 to be easily pulled off by the practitioner. Alternatively, a single fracture line may be provided, preferably intermediate to the illustrated lines 57 or alternatively elsewhere, for example radiating outwardly from the window for a short distance, and preferably extending to the edge 130, for opening up the tray at least in the vicinity of the window. Optionally, a tab 52 may be formed at one end of the strip 53 to facilitate grasping of the same so that the strip may be pulled off more efficiently.

Alternatively, the windows 50 may be used as targets for marking the parts 60 of the teeth onto which the brackets 70 are to be bonded. Thus, a suitable marking implement such as a pen, pencil, printing pad or the like, for example, may be used to mark the area exposed by the window 50, in ink for example, this mark delineating the position required for the bracket 70, for each tooth. Once the parts 60 have been appropriately marked, the tray 100 may be removed from the arch 200. Thereafter, each bracket 70 may be positioned and bonded onto the appropriate part 60 by placing the bracket in registry with the corresponding mark, the bracket 70 and/or the part 60 having previously been provided with a suitable adhesive, and where appropriate curing the adhesive.

Figure 6:
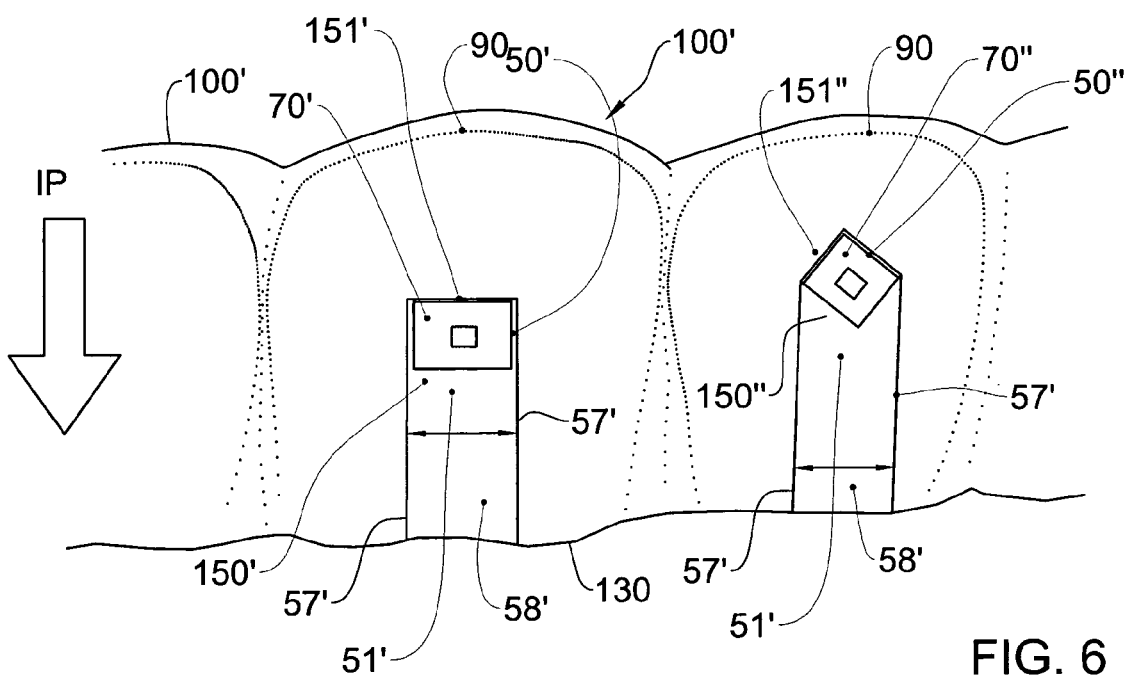
FIG. 6 illustrates in partial side view a second embodiment of the invention.

Referring to FIG. 6, in a second embodiment of the invention the tray 100' comprises all the elements and features of the first embodiment, as described herein mutatis mutandis, with the following difference. In the second embodiment, the tray 100' comprises slots 58' that are integrally formed with the windows 50'. The width of the slot 58' is substantially equivalent to the projected width w' of the bracket taken along the insertion path IP of the tray 100', and the edges 57' of the slot 58' are substantially parallel to this path, preferably. Optionally, the edges 57' may be flared, in a preferably divergent manner towards the free edge 130, but possibly also convergent manner, from the window 50'. In this embodiment, the window 50' has an open end 51', and further comprises target indicators in the form of abutment edges that are sufficient to enable the corresponding bracket to be spatially fixed in two dimensions, i.e., over the surface of the corresponding tooth when the tray is seated thereon. For example, and referring to FIG. 6, where a rectangular bracket 70' is to be fixed at a position where two of the sides thereof are substantially parallel to the insertion path of the tray 100', the corresponding window 150' comprises a single abutment edge 151' to define the position and orientation of the bracket 70' along the direction of the insertion path. The width w' of the window 150' ensures that the bracket position in the direction orthogonal to the insertion path is fixed. Where a rectangular bracket 70" is to is to be fixed at a position where none of the sides thereof are substantially parallel to the insertion path of the tray 100', the corresponding window 150" comprises two abutment edges 151" to define the position and orientation of the bracket 70" along and orthogonal to the direction of the insertion path. Brackets of other shapes require one or more abutment edges, according to the geometry of the brackets.

The tray 100' according to the second embodiment may be designed and manufactured in a similar manner to that described herein for the first embodiment, mutatis mutandis, with the difference that rather than just the windows, the windows are formed with the aforesaid slots, either concurrently, or after the windows are formed.

The tray 100' according to this embodiment may also be used in a similar manner to that described for the first embodiment, mutatis mutandis, with the difference that each bracket is positioned with respect to the corresponding abutment edges of the window. Removal of the tray 100' is simply by lifting the tray 100' away from the arch 200 in a direction opposed to the insertion path. Where the tray 100' is used to mark the area 60, this part plus another portion of the tooth exposed by the slot 58' may be marked in a similar manner to that described for window 50 of the first embodiment. Alternatively, only the appropriate abutment edges need to be marked, as these provide sufficient targeting information for each bracket. Once the teeth are marked thus, each bracket may be positioned and bonded onto the appropriate part of the tooth by placing the bracket in registry with the corresponding mark, the bracket and/or the part 60 having previously been provided with a suitable adhesive, and where appropriate curing the adhesive.

Figure 7:
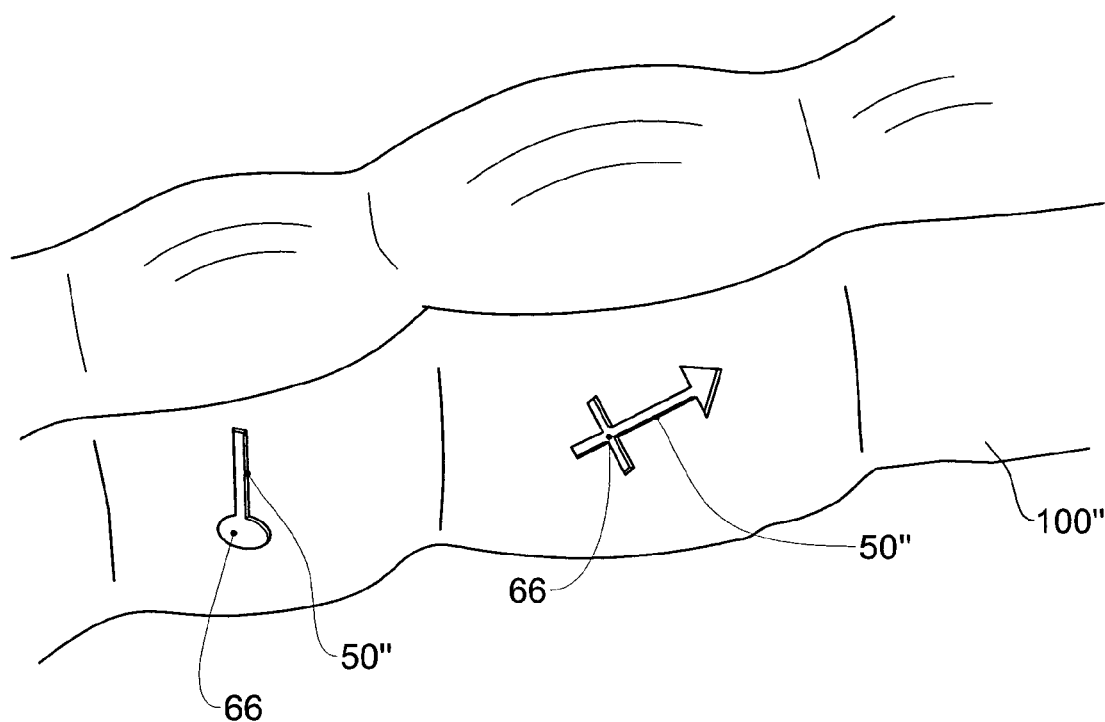
FIG. 7 illustrates in partial isometric view a third embodiment of the invention.
Figure 8A:
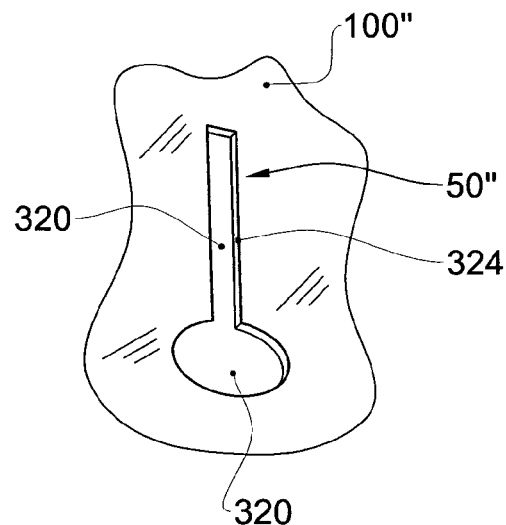
FIGS. 8a, 8b, 8c, 8d and 8e illustrate alternative window configurations for the embodiment of FIG. 7.

Referring to FIG. 7, a third embodiment of the invention the tray 100" comprises all the elements and features of the first embodiment, as described herein mutatis mutandis, with the following difference. In the third embodiment, the tray 100", rather than the windows being in a form complementary to the shape of the brackets, the windows 50" are of a shape that allow the corresponding parts 60 to be marked in a manner that permits the brackets 70 to be subsequently targeted after the tray 100" is removed. Thus, windows 50" may be in the form of a symbol, for example slits such as cross-hairs "+" or "X", which act as indirect target indicators. For example, and referring to FIG. 8a, a window 50" may be in the form of a slit 310 in the shape of an arrow 314 and having a cross-member 315 intersecting this at 316. The intersection point 316 is representative of the center of the bracket, while arrow 314 points the direction of a datum reference line of the bracket.

Figure 8B:
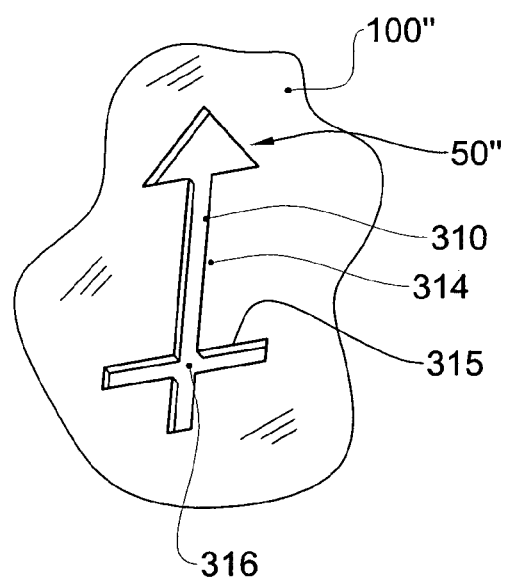

In another example illustrated in FIG. 8b window 50" may be in the form of a slit 320 in the shape of a line 324 and having a disc at 326. The disc 326 is representative of the center of the bracket, while line 324 points the direction of a datum line of the bracket. Many other forms are possible for the window 50".

Figure 8C:
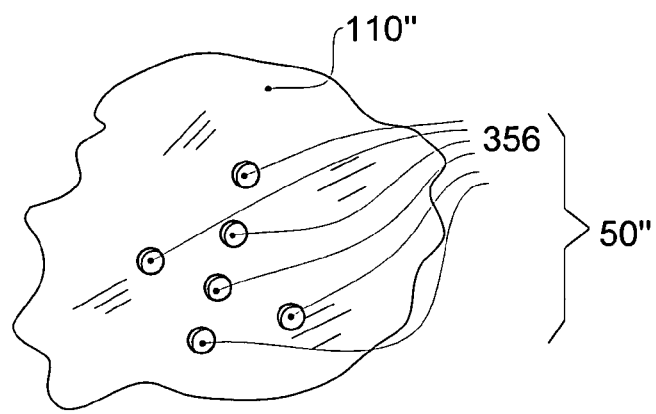

Alternatively, and as illustrated in FIG. 8c, a plurality of windows 356, each in the shape of a slot or round hole, for example, are provided, and provided in a recognizable pattern. Together, the windows 356 define the spatial location and orientation of the bracket. Any marking method may be used to mark the tooth surface via the windows 356—for example, ink, or by using a sharp instruments through the windows 356 to scratch the tooth surface. When the shell is removed, the markings are left behind, and the appropriate bracket can be aligned with respect to the marks.

Figure 8D:
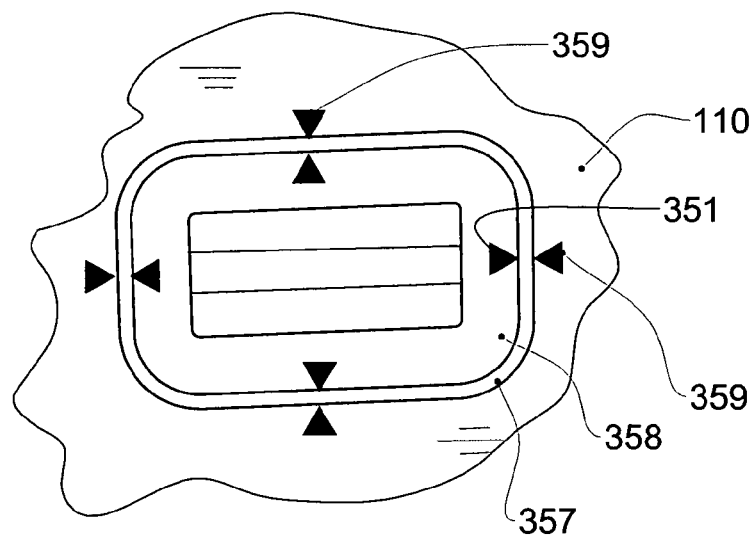

Alternatively, and as illustrated in FIG. 8d, the window 357 may be of a size greater than the bracket 358, and comprise appropriate markings 359 along the periphery of the window 357. The markings 359 may be transferred to the tooth surface manually by scratching the tooth or otherwise marking the same with ink or the like at locations juxtaposed to the markings, and when the shell 110 is removed, the bracket is aligned with respect to these marks. For this purpose, the bracket 358 is advantageously provided width alignment marks 351 which are arranged to match the positions of marks 359. Alternatively, the bracket 358 may be aligned directly with the markings 359 while the shell is on the arch 200, and after bonding the tray 110 is removed.

Figure 9:
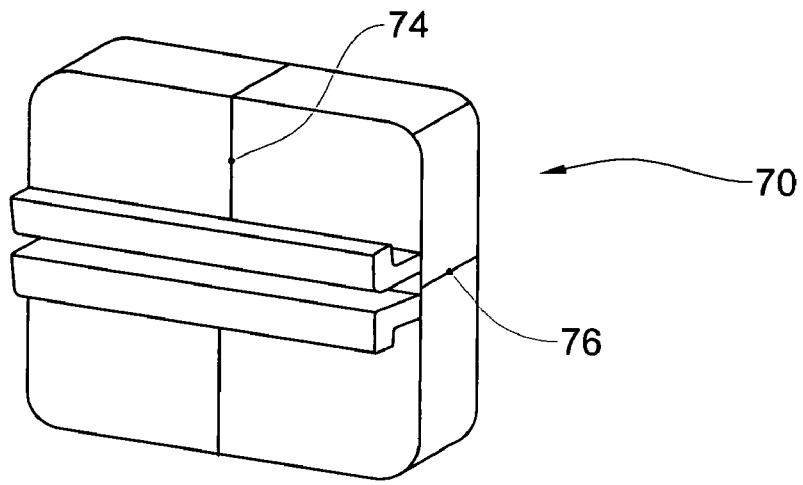
FIG. 9 illustrates a typical bracket configuration which may be used with the present invention.

As illustrated in FIG. 9, for example, in each case the brackets 70 may be marked to show a datum centerline 74, bracket slot position 76, or other geometrical references or datum references of the bracket.

The tray 100" according to the third embodiment may be designed and manufactured in a similar manner to that described herein for the first embodiment, mutatis mutandis, with the difference that rather than windows 50, the windows 50" are formed instead.

Figure 8E:
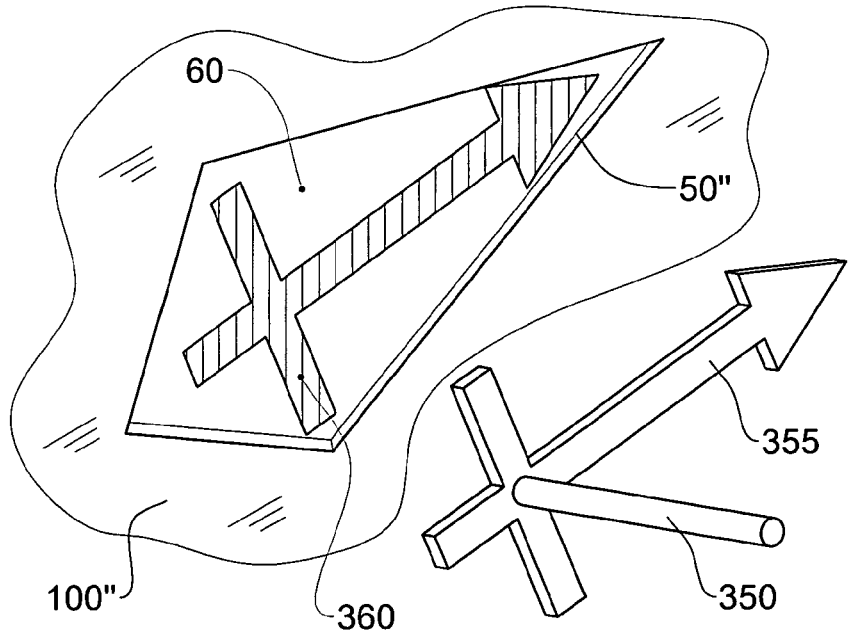

The tray 100" according to this embodiment may also be used in a similar manner to that described for the first embodiment where the positions of the brackets are marked by means of the tray, mutatis mutandis. Thus, the tray 100" is seated onto the arch 200 so that the windows 50" are superposed or in registry with the corresponding parts 60 onto which the brackets 70 are eventually to be positioned, leaving exposed a small area 66 of this part in the shape of the corresponding window 50". This area 66 may be marked in a similar manner to that described for window 50 of the first embodiment, for example by means of a fine pen or pencil or the like, or for example by using a coloring pad. Such a pad may hold a quantity of ink or other pigment, and when brought into contact with the outside of the tray 100" in the vicinity of each window 50", the color or pigment only colors the exposed area 66 of the corresponding tooth. Alternatively, the window is of a predetermined shape, for example the shape of as kite, as illustrated in FIG. 8e, and a printing implement in the form of a wand 350 having at its extremity a printing pad 355 of an appropriate shape is used to mark the part 60 with a targeting mark 360. In such a case, the window 50" is used to enable the printing pad to be properly oriented and positioned with respect to the tray 100", and in turn the printing pad comprises a printing symbol that is indicative of position and orientation of the bracket that it is desired to place there. Such a symbol may be similar, for example, to the shapes of the windows described in respect of FIGS. 8a to 8d. Thus, once the teeth are marked via the windows 50", these markings provide sufficient targeting information for each bracket. The tray 100" is then removed by lifting the tray 100" away from the arch 200 in a direction opposed to the insertion path. Then each bracket may be positioned and bonded onto the appropriate part of the tooth by placing and aligning the bracket in registry with the corresponding mark, the bracket and/or the part 60 having previously been provided with a suitable adhesive, and where appropriate curing the adhesive.

The tray 100" according to the third embodiment is particularly advantageous since it permits the choice of actual bracket to be deferred if necessary, for example due to logistical problems in obtaining specific marks of brackets. Since the positional data required for the bracket is marked using the tray 100", it is possible to target any bracket to a particular target marked with the tray 100", so long as the bracket comprises suitable datums compatible with the marking criteria used for the target symbol, for example centerline and slot location datums.

Figure 10:
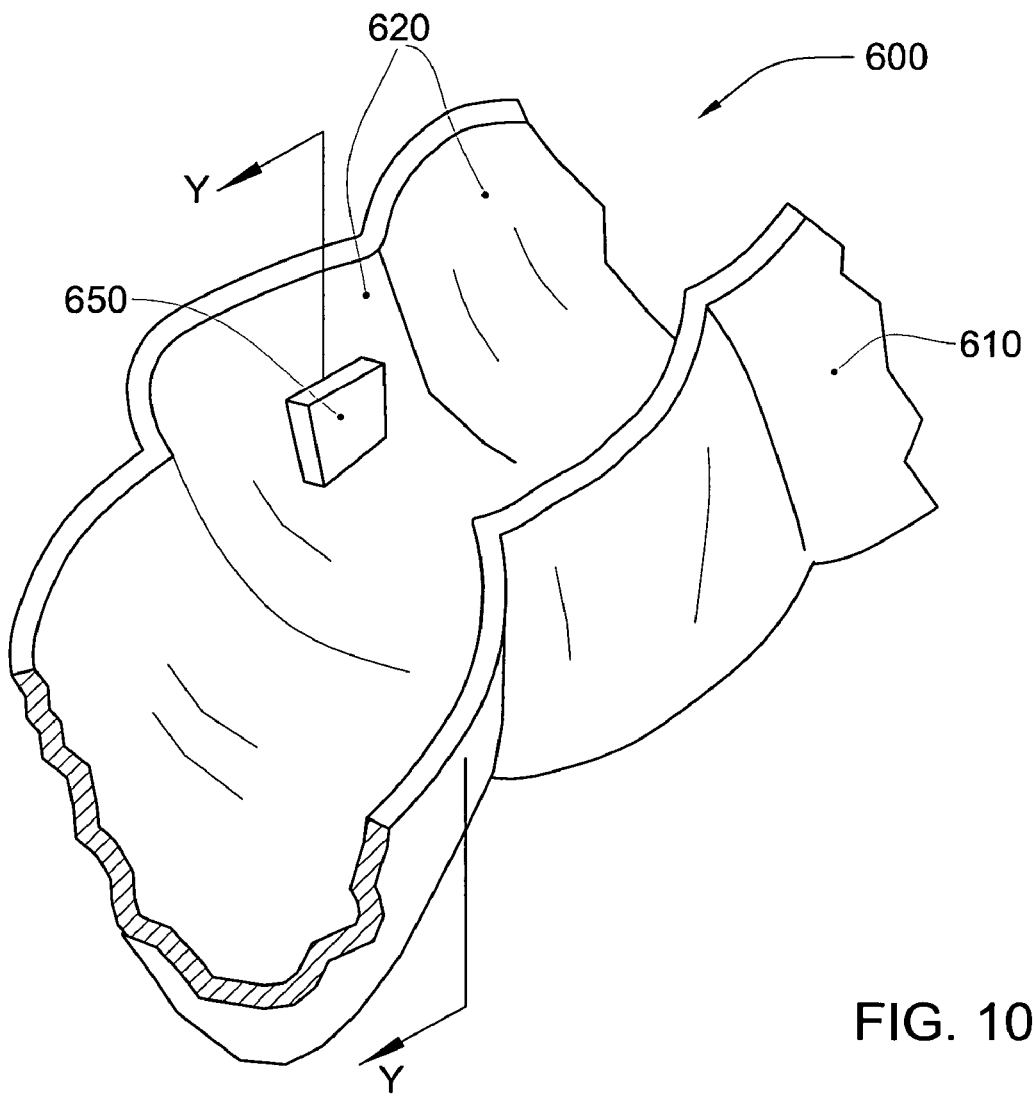
FIG. 10 is a fragmented isometric view of a fourth embodiment of the invention.
Figure 11:
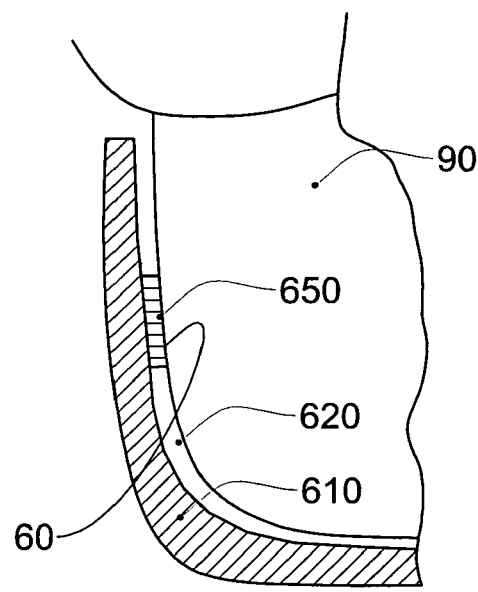
FIG. 11 shows in partial cross-sectional view the embodiment of FIG. 10 along Y-Y.

Referring to FIG. 10, in a fourth embodiment of the invention the tray 600 comprises all the elements and features of the other embodiment, as described herein mutatis mutandis, with the following difference. In the fourth embodiment, the tray 600 comprises a shell 610 similar to shell 110 of the previous embodiments, but does not comprise windows. Rather, transfer means 650 are provided in the inside of the cavities 620 to transfer target information to the corresponding tooth regarding where the bracket 70 is to be located and bonded. As illustrated in FIG. 11, the transfer means 650 may comprise a pad or the like containing a transfer material including, for example, ink or other staining pigment, or an etching acid or the like, for example. Thus, when the appropriate tooth is received in the cavity containing the pad, the pad can be pressed against the tooth, transferring or printing thereon the transfer material in the shape of the pad and in the correct position with respect to the tooth. The pad may be in a form complementary to the shape of the brackets, and thus allow the corresponding parts 60 to be marked in a manner that permits the brackets 70 to be subsequently targeted after the tray 600 is removed. Alternatively, the pads may be in the form of a symbol, for example cross-hairs in the form of "+" or "X", or a series of dots or lines in a recognizable pattern, or arrows, or any other suitable shape, which act as indirect target indicators. When the shell is removed, the markings are left behind, and the appropriate bracket can be aligned with respect to the marks.

Alternatively, the transfer pad may contain a transfer patch of a suitable material that is transferred to the tooth. The transfer patch may comprise an adhesive label that is transferred to the tooth. The adhesive label may be, for example, in the shape of the periphery of the required bracket, so that the bracket may be fitted in the open area in the patch after the patch is adhered to the tooth. The adhesive patch may comprise a chemical or light-cured adhesive, which sets when the tooth has been properly seated in the appropriate cavity and the patch aligned on the tooth. Alternatively, the patch may be a series of dots or lines which together define the spatial location and orientation of the bracket. Alternatively, the patch may comprise adhesive on both sides thereof, enabling the patch to first bond onto the tooth, and then allow the bracket to be bonded to the patch. Accordingly, it may be convenient to have different adhesives for each of the sides, and such that each adhesive may be selectively activated independently of the other. For example, the adhesives may be light-curing adhesives, each of which cures at a different wavelength. This facilitates the procedure of bonding the patch to the tooth first, and then allowing the bracket to be bonded to the patch. Advantageously, the patch may be in the form or shape of the bracket, or in any other suitable shape such as to guide the bracket to the required alignment with respect thereto and thus the tooth.

Figure 12:
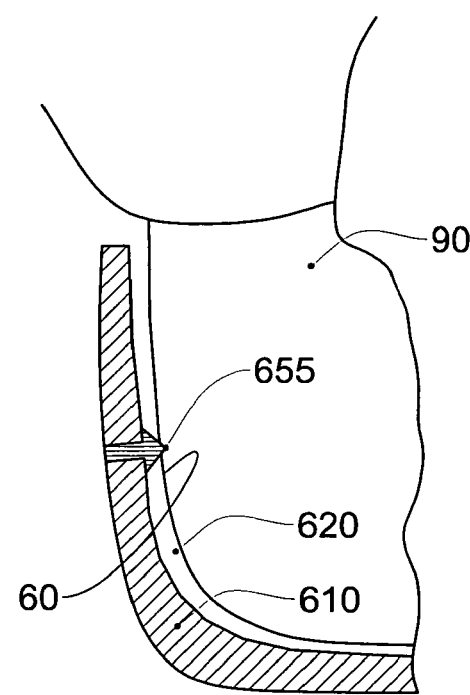
FIG. 12 shows in partial cross-sectional view an alternative configuration for embodiment of FIG. 10 along Y-Y.

Alternatively, and as illustrated in FIG. 12, the transfer means may comprise a sharp protrusion 655 of appropriate shape and size. Thus, when the appropriate tooth is received in the cavity 620 containing the protrusion, this can be pressed against the tooth 90, scratching thereon marks in the shape of the protrusion and in the correct position with respect to the tooth. The protrusion may be in a form complementary to the shape of the brackets, and thus allow the corresponding parts 60 to be marked in a manner that permits the brackets 70 to be subsequently targeted after the tray 600 is removed. Alternatively, the protrusion may be in the form of a symbol, for example cross-hairs in the form of "+" or "X", or a series of dots or lines in a recognizable pattern, or arrows, or any other suitable shape, which act as indirect target indicators. When the shell is removed, the markings are left behind, and the appropriate bracket can be aligned with respect to the marks.

The tray 600 according to this embodiment may also be used in a similar manner to that described for the other embodiments where the positions of the brackets are marked by means of the tray, mutatis mutandis. Thus, the tray 600 is seated onto the arch 200 so that the transfer means 650 are in registry with the corresponding parts 60 onto which the brackets 70 are eventually to be positioned. The orthodontist then presses the transfer means against the appropriate tooth, leaving a mark or adhesive patch on the area 60, according to the type of transfer mans used. Thus, once the teeth are marked via the transfer means 650, these markings provide sufficient targeting information for each bracket to be aligned on the tooth. The tray 600 is then removed by lifting the tray 600 away from the arch 200 in a direction opposed to the insertion path. Then each bracket may be positioned and bonded onto the appropriate part of the tooth by placing the bracket in registry with the corresponding mark, the bracket and/or the part 60 having previously been provided with a suitable adhesive, and where appropriate curing the adhesive.

The tray 600 according to the this embodiment is also particularly advantageous since it permits the choice of actual bracket to be deferred if necessary, for example due to logistical problems in obtaining specific marks of brackets. Since the positional data required for the bracket is marked using the tray 600, it is possible to target any bracket to a particular target marked with the tray 600, so long as the bracket comprises suitable datums compatible with the marking criteria used for the target symbol, for example centerline and slot location datums.

The tray 600 according to this embodiment may be manufactured in a similar manner to that described above for the other embodiments with the following differences, mutatis mutandis. Rather than comprising windows, the tray according to this embodiment is provided with the transfer means 650, typically after the basic shell 610 has been fabricated, but optionally also integrally therewith. For example, once the basic shell 610 is manufactured using CNC methods, the appropriate transfer means 650 are located in the shell using any suitable computer controlled or other navigation technique for locating the means in their correct positions. Alternatively, the transfer means may be temporarily mounted onto a positive tooth model, and then the tray is vacuum formed over the model, so that when the tray is removed, the transfer means are carried by the tray.

In yet other embodiments, the tray may comprise any combination and permutation of windows according to the first embodiment, and/of the windows according to the second embodiment, and/or the windows according to the third embodiment, and/or of the transfer means of the fourth embodiment, mutatis mutandis.

Figure 13:
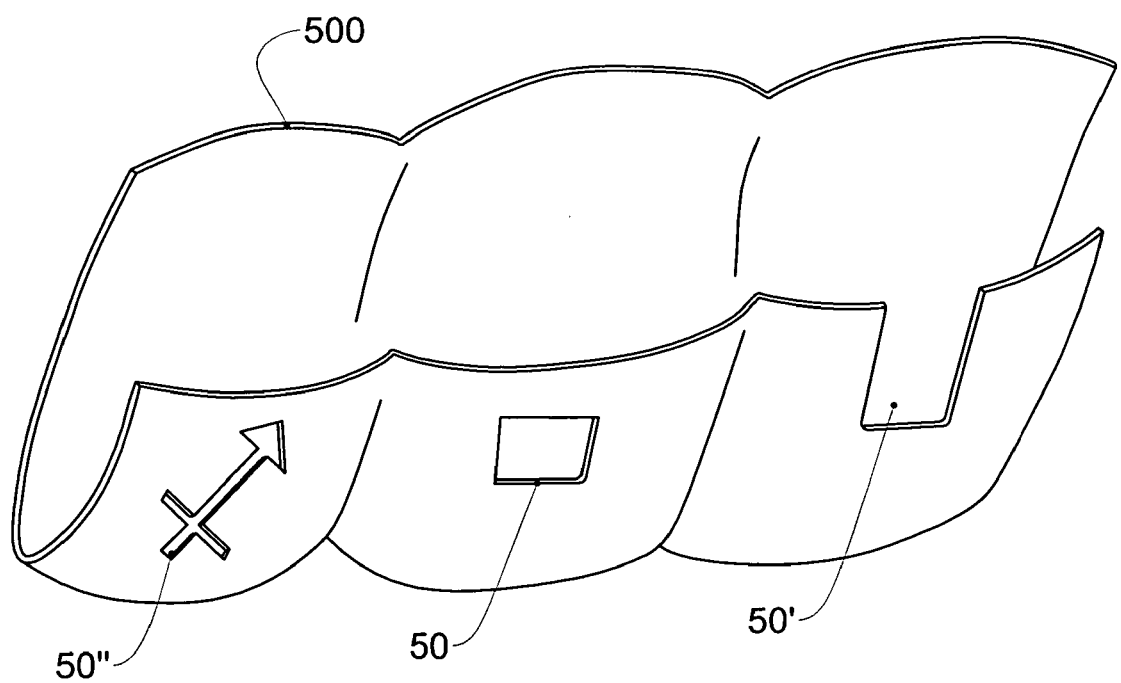
FIG. 13 illustrates in isometric view a fifth embodiment of the invention.

Referring to FIG. 13, in a fifth embodiment of the invention a tray 500 is provided which is substantially similar to a portion of the full tray according to any of the other embodiments described herein. The tray 500 thus comprises all the elements and features of these embodiments, as described herein mutatis mutandis, wherein the tray portion 500 is adapted to be placed over one or several teeth, rather than over the full arch 200. In the fourth embodiment, the tray 500 may comprise any one of or a combination of the windows according to any embodiment. For example, as illustrated in FIG. 13, the tray 500 is adapted to be seated over three adjacent teeth, and comprises windows 50, 50' and 50".

The tray 500 according to the fifth embodiment may be designed and manufactured in a similar manner to that described herein for the first, second, third or fourth embodiments, mutatis mutandis, with the difference that rather than a complete tray, only the relevant part of the tray is formed instead.

The tray 500 according to this embodiment may also be used in a similar manner to that described for the first, second, third or fourth embodiments, mutatis mutandis. Thus, the tray 500 is seated onto the appropriate teeth of arch 200 so that the windows are in registry with the corresponding parts 60 of the teeth onto which the brackets 70 are eventually to be positioned. Thereafter, the brackets may be targeted onto these parts directly via the windows, or indirectly by using the windows to mark the teeth in an appropriate manner, or by marking the positions of the brackets as described for the fourth embodiment, and bonded onto the teeth. The tray 500 is removed by lifting the same away from the arch 200 in a direction opposed to the insertion path.

The tray 500 according to the fifth embodiment is particularly useful in permitting brackets to be placed in only one or some of the teeth without the necessity of providing a full tray. Such a capability is of particular advantage when it is desired to add or replace a number of brackets to the teeth after the teeth have been moved by some amount.

When the tray 500 is for a single tooth it may not even be necessary to provide another model of the dentition (physical or virtual). Relative to the tooth, the bracket remains in the same position during the full duration of the treatment. Since the tray 500 comprises a cavity that substantially follows the shape of the tooth it is designed to fit over, the window of the tray will remain in the appropriate place with respect to the tooth when the tray 500 is properly seated onto the appropriate tooth. Thus, the original tooth model may be used to provide the geometrical information required to produce the tray 500.

In some embodiments it may be desired to position more than one dental appliance thereon, each at a predetermined position and orientation, in which case a number of windows, each corresponding to a different appliance, are made in a suitable tray, similarly to the manner described above relating to a single window per tooth, mutatis mutandis.

In every embodiment, it is possible to mark the tray with useful information including, for example, at least one of: the name of the patient; the name of the orthodontist; the name of the dental lab that manufactured the tray; the date of manufacture; the model, type, serial numbers, or other identifying references for the brackets; and so on.

In the method claims that follow, alphanumeric characters and Roman numerals used to designate claim steps are provided for convenience only and do not imply any particular order of performing the steps.

Finally, it should be noted that the word "comprising" as used throughout the appended claims is to be interpreted to mean "including but not limited to".

While there has been shown and disclosed exemplary embodiments in accordance with the invention, it will be appreciated that many changes may be made therein without departing from the spirit of the invention.

The invention claimed is:

1. A targeting device for enabling one or more orthodontic elements to be positioned with respect to at least one tooth in a predetermined manner and to be bonded thereonto at such a position, comprising:
   a shell comprising, for the or each tooth with respect to which it is desired to align a orthodontic element, a cavity shaped to receive the tooth, and further comprising targeting indicators configured for enabling the corresponding said orthodontic element to be guided into alignment in said predetermined manner with respect to a said tooth that is received in a corresponding said cavity, wherein said targeting indicators are associated with windows comprised in said shell, each window extending from an outside of said shell to a corresponding said cavity,
   wherein for at least one window, at least one of:
   at least a part of the periphery of said window comprises said target indicators, wherein said target indicators are in the form of visual markings with respect to which predetermined reference datums on a corresponding said orthodontic element are to be aligned;
   the window is of a shape indicative of the said manner in which the corresponding said orthodontic element is to be fixed with respect to the corresponding tooth surface;
   at least part of the edges of said window comprise said target indicators, wherein said parts of said edges are of a shape substantially complementary to the plan profile of corresponding parts said orthodontic element.

2. A device according to claim 1, wherein said predetermined manner includes a predetermined position and a predetermined orientation with respect to a corresponding tooth surface of a said tooth.

3. A device according to claim 1, wherein each said window is configured for enabling the corresponding orthodontic element to be attached to a corresponding said tooth surface.

4. A device according to claim 3, wherein each said window is configured for enabling the corresponding orthodontic element to subsequently remain attached thereat in the absence of said device.

5. A device according to claim 1, wherein each said window is sufficiently large to provide a clearance with respect to a said orthodontic element that is targeted via said window.

6. A device according to claim 1, wherein each said window is configured for enabling a corresponding said orthodontic element to be positioned in said predetermined manner with respect to a surface of a tooth in a non-engaging manner with respect to the shell.

7. A device according to claim 1, wherein said target indicators are provided in at least one said cavity and interact with a tooth that is received in said cavity such as to mark thereon the said desired manner in which it is desired to align a said orthodontic element with respect to the tooth.

8. A targeting device for enabling one or more orthodontic elements to be positioned with respect to at least one tooth in a predetermined manner and to be bonded thereonto at such a position, comprising:
   a shell comprising, for the or each tooth with respect to which it is desired to align a orthodontic element, a cavity shaped to receive the tooth, and further comprising targeting indicators configured for enabling the corresponding said orthodontic element to be guided into alignment in said predetermined manner with respect to a said tooth that is received in a corresponding said cavity
   wherein said target indicators comprise a transfer patch having a form correlated to said predetermined manner, such that when a tooth is received in said cavity, the transfer patch transfers a material to said tooth, wherein the shape of said transferred material is correlated to the desired manner in which it is desired to align the corresponding orthodontic element; and
   wherein said target indicators comprise a transfer patch having a form correlated to said predetermined manner, such that when a tooth is received in said cavity, the transfer patch transfers a material to said tooth, wherein the shape of said transferred material is correlated to the desired manner in which it is desired to align the corresponding orthodontic element.

9. A device according to claim 8, wherein said transfer patch is configured such as to at least one of:
   to transfer a sticker of predetermined shape to a tooth received in said cavity;
   to transfer a colored pigment in a predetermined shape to a tooth received in said cavity;
   to transfer an etching material in a predetermined shape to a tooth received in said cavity, wherein said target indicators comprise a protrusion having a form correlated to said predetermined manner, such that when a tooth is received in said cavity, the protrusion can form marks on the surface of the tooth in contact therewith, wherein the shape of said protrusions is such that the said marks are correlated to the desired manner in which it is desired to align the corresponding orthodontic element.

10. A method for aligning and bonding one or more orthodontic elements with respect to at least one tooth in a predetermined manner, comprising:
   (A) providing target indicators for the or each tooth that it is desired to align a said orthodontic element with, and for said each orthodontic element in turn:
   (B) bringing said orthodontic element into proximity with corresponding said targeting indicators; and
   (C) aligning said orthodontic element with respect to said targeting indicators to achieve the required said alignment of the element with respect to the tooth;
   (D) providing a shell comprising, for the or each tooth that it is desired to align a said orthodontic element with, a cavity shaped to receive the tooth, and further comprising targeting indicators configured for guiding the or each said orthodontic element into alignment in said predetermined manner with respect to a said tooth that is received in a corresponding said cavity;
   (E) seating said shell over said tooth such that the or each said tooth is received in a respective said cavity; and for said each orthodontic element in turn:
   (F) bringing said orthodontic element into proximity with corresponding said targeting indicators; and
   (G) aligning said orthodontic element with respect to said targeting indicators to achieve the required said alignment of the element with respect to the tooth accommodated in the corresponding said cavity, wherein said targeting indicators are associated with windows comprised in said shell, each said window extending from an outside of said shell to a corresponding said cavity, and wherein step (D) comprises inserting a said orthodontic element into a said window into contact with a said tooth accommodated in the corresponding said cavity, wherein the shape, location and orientation of the window is complementary to the shape and desired location and orientation of the said orthodontic element with respect to the said tooth.

11. A method according to claim 10, further comprising the step of bonding each said orthodontic element when aligned in said predetermined manner with respect to the corresponding tooth, and the step of removing the said shell after the said orthodontic elements have been bonded to the teeth.

12. A method for aligning and bonding one or more orthodontic elements with respect to at least one tooth in a predetermined manner, comprising:
(A) providing target indicators for the or each tooth that it is desired to align a said orthodontic element with, and for said each orthodontic element in turn:
(B) bringing said orthodontic element into proximity with corresponding said targeting indicators; and
(C) aligning said orthodontic element with respect to said targeting indicators to achieve the required said alignment of the element with respect to the tooth
(D) providing a shell comprising, for the or each tooth that it is desired to align a said orthodontic element with, a cavity shaped to receive the tooth, and further comprising targeting indicators configured for guiding the or each said orthodontic element into alignment in said predetermined manner with respect to a said tooth that is received in a corresponding said cavity;
(E) seating said shell over said tooth such that the or each said tooth is received in a respective said cavity; and for said each orthodontic element in turn:
(F) bringing said orthodontic element into proximity with corresponding said targeting indicators; and
(G) aligning said orthodontic element with respect to said targeting indicators to achieve the required said alignment of the element with respect to the tooth accommodated in the corresponding said cavity,
wherein said targeting indicators are associated with windows comprised in said shell, each said window extending from an outside of said shell to a corresponding said cavity, and
wherein step (D) comprises marking the desired position and orientation of a said orthodontic element with respect to a said tooth accommodated in the corresponding said cavity by means of said corresponding window, wherein the location and orientation of the window is complementary to the shape and desired location and orientation of the said orthodontic element with respect to the said tooth.

13. A method according to claim 12, wherein the shape of the window is complementary to the shape of the orthodontic element that it is desired to align with respect to said tooth.

14. A method according to claim 13, further comprising the step of removing the shell and aligning each said orthodontic element with the corresponding marked position on the corresponding tooth.

15. A method according to claim 14, further comprising the step of bonding each said orthodontic element when aligned in said predetermined manner with respect to the corresponding tooth.

16. A method for aligning and bonding one or more orthodontic elements with respect to at least one tooth in a predetermined manner, comprising:
(A) providing target indicators for the or each tooth that it is desired to align a said orthodontic element with, and for said each orthodontic element in turn:
(B) bringing said orthodontic element into proximity with corresponding said targeting indicators; and
(C) aligning said orthodontic element with respect to said targeting indicators to achieve the required said alignment of the element with respect to the tooth
(D) providing a shell comprising, for the or each tooth that it is desired to align a said orthodontic element with, a cavity shaped to receive the tooth, and further comprising targeting indicators configured for guiding the or each said orthodontic element into alignment in said predetermined manner with respect to a said tooth that is received in a corresponding said cavity;
(E) seating said shell over said tooth such that the or each said tooth is received in a respective said cavity; and for said each orthodontic element in turn:
(F) bringing said orthodontic element into proximity with corresponding said targeting indicators; and
(G) aligning said orthodontic element with respect to said targeting indicators to achieve the required said alignment of the element with respect to the tooth accommodated in the corresponding said cavity,
wherein said targeting indicators are associated with windows comprised in said shell, each said window extending from an outside of said shell to a corresponding said cavity,
wherein said predetermined manner includes aligning one or more said orthodontic elements with respect to said at least one tooth in a predetermined position and orientation,
wherein said target indicators comprise a transfer patch having a form correlated to said predetermined manner, and
wherein step (D) comprises transferring a transfer material to a said tooth that is accommodated in a corresponding said cavity, wherein the shape of said transferred material is correlated to the desired manner in which it is desired to align the corresponding orthodontic element.

17. A method according to claim 16, wherein said transfer patch transfers at least one of: a sticker of predetermined shape to a tooth received in said cavity; a colored pigment in a predetermined shape to a tooth received in said cavity; an etching material in a predetermined shape to a tooth received in said cavity.

18. A method for aligning and bonding one or more orthodontic elements with respect to at least one tooth in a predetermined manner, comprising:
(A) providing target indicators for the or each tooth that it is desired to align a said orthodontic element with, and for said each orthodontic element in turn:
(B) bringing said orthodontic element into proximity with corresponding said targeting indicators; and
(C) aligning said orthodontic element with respect to said targeting indicators to achieve the required said alignment of the element with respect to the tooth
(D) providing a shell comprising, for the or each tooth that it is desired to align a said orthodontic element with, a cavity shaped to receive the tooth, and further comprising targeting indicators configured for guiding the or each said orthodontic element into alignment in said predetermined manner with respect to a said tooth that is received in a corresponding said cavity;

(E) seating said shell over said tooth such that the or each said tooth is received in a respective said cavity; and for said each orthodontic element in turn:

(F) bringing said orthodontic element into proximity with corresponding said targeting indicators; and (G) aligning said orthodontic element with respect to said targeting indicators to achieve the required said alignment of the element with respect to the tooth accommodated in the corresponding said cavity, wherein said targeting indicators are associated with windows comprised in said shell, each said window extending from an outside of said shell to a corresponding said cavity, wherein said predetermined manner includes aligning one or more said orthodontic elements with respect to said at least one tooth in a predetermined position and orientation, wherein said target indicators comprise a protrusion having a form correlated to said predetermined manner, and wherein step (D) comprises causing said protrusion to come into contact with a tooth accommodated in a corresponding said cavity and to form marks on the surface of the tooth in contact therewith, wherein the shape of said protrusions is such that the said marks are correlated to the desired manner in which it is desired to align the corresponding orthodontic element.

* * * * *